United States Patent
Imperiale-Hagerman

(10) Patent No.: US 10,806,123 B2
(45) Date of Patent: Oct. 20, 2020

(54) METHODS OF PROVIDING GRASS GROWTH AND NEMATODE SUITABILITY INDICES TO ASSIST DETERMINATION OF TIMING OF PARASITICIDE TREATMENT

(71) Applicant: BOEHRINGER INGELHEIM ANIMAL HEALTH USA INC., Duluth, GA (US)

(72) Inventor: Stephen Mario Imperiale-Hagerman, Calabasas, CA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 952 days.

(21) Appl. No.: 15/378,729

(22) Filed: Dec. 14, 2016

(65) Prior Publication Data

US 2017/0181403 A1    Jun. 29, 2017

Related U.S. Application Data

(60) Provisional application No. 62/272,062, filed on Dec. 28, 2015.

(51) Int. Cl.
*A01K 13/00* (2006.01)
*G16B 5/00* (2019.01)
(Continued)

(52) U.S. Cl.
CPC ............ *A01K 13/003* (2013.01); *A01K 29/00* (2013.01); *G06Q 10/04* (2013.01);
(Continued)

(58) Field of Classification Search
CPC ............................... A01K 13/00; G06Q 10/04
(Continued)

(56) References Cited

U.S. PATENT DOCUMENTS

| 7,212,922 B1 | 5/2007 | Longacre et al. |
| 2002/0016676 A1 | 2/2002 | Sann |

(Continued)

FOREIGN PATENT DOCUMENTS

EP    2 874 072 A1    11/2013

OTHER PUBLICATIONS

Duru, M. et al., "Modeling above-ground herbage mass for a wide range of grassland community types," Ecological Modelling vol. 220, pp. 209-225 (2008).
(Continued)

*Primary Examiner* — David R Vincent
(74) *Attorney, Agent, or Firm* — John Ezcurra

(57) ABSTRACT

The present invention builds and conveys to users in need thereof a Grass Growth Index (GGI) and a Nematode Suitability Index (NSI), to assist the determination of whether and when to administer parasiticides to grazing livestock, such as bovine, ovine and caprine animals. In particular, the invention relates to a computer-implemented method whereby GGI and NSI are calculated based upon both user-supplied information (e.g. grass/forage type and location data) and user-independent information (e.g. weather and environmental condition data associated with the location over time, and grass and nematode growth parameters). Importantly, the disclosed methods provide users with information as to when and where their herds of grazing animals may be at the greatest risk of parasite infestation.

11 Claims, 2 Drawing Sheets

(51) Int. Cl.
    *G16B 45/00*     (2019.01)
    *G06Q 10/06*     (2012.01)
    *G06Q 50/02*     (2012.01)
    *G06Q 10/04*     (2012.01)
    *A01K 29/00*     (2006.01)
    *G06F 16/29*     (2019.01)

(52) U.S. Cl.
    CPC ......... *G06Q 10/0637* (2013.01); *G06Q 50/02* (2013.01); *G16B 5/00* (2019.02); *G16B 45/00* (2019.02); *G06F 16/29* (2019.01)

(58) Field of Classification Search
    USPC ...................................................... 706/15, 45
    See application file for complete search history.

(56) References Cited

U.S. PATENT DOCUMENTS

| | | |
|---|---|---|
| 2007/0282112 A1 | 12/2007 | Chou et al. |
| 2010/0306012 A1 | 12/2010 | Zyskowski et al. |
| 2011/0295575 A1 | 12/2011 | Levine et al. |
| 2012/0283094 A1* | 11/2012 | Meng ..................... A01N 43/56 504/100 |
| 2014/0207523 A1 | 7/2014 | Leachman et al. |
| 2015/0070188 A1 | 3/2015 | Aramburu |
| 2015/0112595 A1 | 4/2015 | Brehmer et al. |

OTHER PUBLICATIONS

McCall, D.G. et al. "A pasture growth model for use in a whole-farm dairy production model," Agricultural Systems, vol. 76, pp. 1183-1205 (2003).

Written Opinion of the International Searching Authority for PCT/US2016/066590, international filing date Dec. 14, 2016, dated Jul. 12, 2018.

\* cited by examiner

METHODS OF PROVIDING GRASS GROWTH AND NEMATODE SUITABILITY INDICES TO ASSIST DETERMINATION OF TIMING OF PARASITICIDE TREATMENT

CROSS-REFERENCE TO RELATED APPLICATIONS

This application claims priority to U.S. provisional patent application Ser. No. 62/272,062, filed on 28 Dec. 2015, the disclosure of which is herein incorporated by reference in its entirety.

FIELD OF THE INVENTION

The invention generally relates to computer-implemented methods of providing users with grass growth and nematode suitability indices, for the purpose of assisting the user with the determination of whether and when to administer parasiticides to grazing animals, such as bovines, ovines, caprines and the like. In particular, the methods comprises the steps of receiving user inputs (e.g. forage type data and location data), identifying weather and environmental condition data associated with the user-provide location, identifying growth parameters for both the forage type and the nematodes and calculating grass growth and nematode suitability indices based upon the identified and user-supplied information.

BACKGROUND OF THE INVENTION

Internal parasites of grazing animals especially sheep, goats, and cattle are a direct threat to the economics of meat production as the internal parasites especially worms (helminths) rob the young animal of nutrients, reducing potential weight gain. The life cycle of worms, in general: infective larvae are ingested by the animal; the larvae become adults within the animal and lay their eggs in the animal's digestive tract which are then passed to the pasture. The eggs hatch outside the animal and the larvae develop to the infective 3rd stage in soil and manure. The larvae are then ingested by animals and the cycle repeats itself. As to nematodes in particular, the parasite first undergoes a series of moults through larval stages (designated L1 to the adult L5 form). Secondly, in most (but not all) nematodes it is the L3 larvae that is the infective form, important exceptions to this being the Ascarids, such as *Ascaris lumbricoides* and the pinworms, where it is either the L1 larvae, or eggs containing L1 or L2 larvae that are infective. Thirdly the L3 form onwards in all species undergoes a migration within the body of the definitive host as it matures into the adult parasite, usually via the bloodstream or lymphatic system to the heart, lungs, trachea, and then to the intestine. Finally, in most cases the parasite leaves the definitive host as thin walled eggs in the feces.

And while there is a continuing need for new agents to manage endoparasitic infestations in livestock animals due to the increasing parasite burden, it is equally important for owners of livestock to know when their valuable assets are at the highest risk of infestation. As such, inventors sought to develop a new tool to assist livestock producers in combatting endoparasites.

SUMMARY OF THE INVENTION

An object of the instant invention is to provide livestock producers with a detailed understanding as to when and where their grazing animals may face the highest burden of internal parasites, particularly nematodes.

In an embodiment, the invention provides as a computer-implemented method for determining and/or conveying a Grass Growth Index (GGI) and a Nematode Suitability Index (NSI), which are used by the livestock producer to determine timing of parasiticide treatments.

The invention naturally encompasses software for carrying out the computer-implemented method. In general, the method requires a network connection, whereby a user can convey certain weather, environmental condition data, and location data to a target computer. The target computer may have loaded thereon, or be capable of accessing from a remote source, non-user supplied information, such as weather and environmental condition data (associated with the user-supplied location), and grass nematode growth parameters. All these and other data are used by the computer to calculate the GGI and NSI.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION OF THE INVENTION

Figure 1:
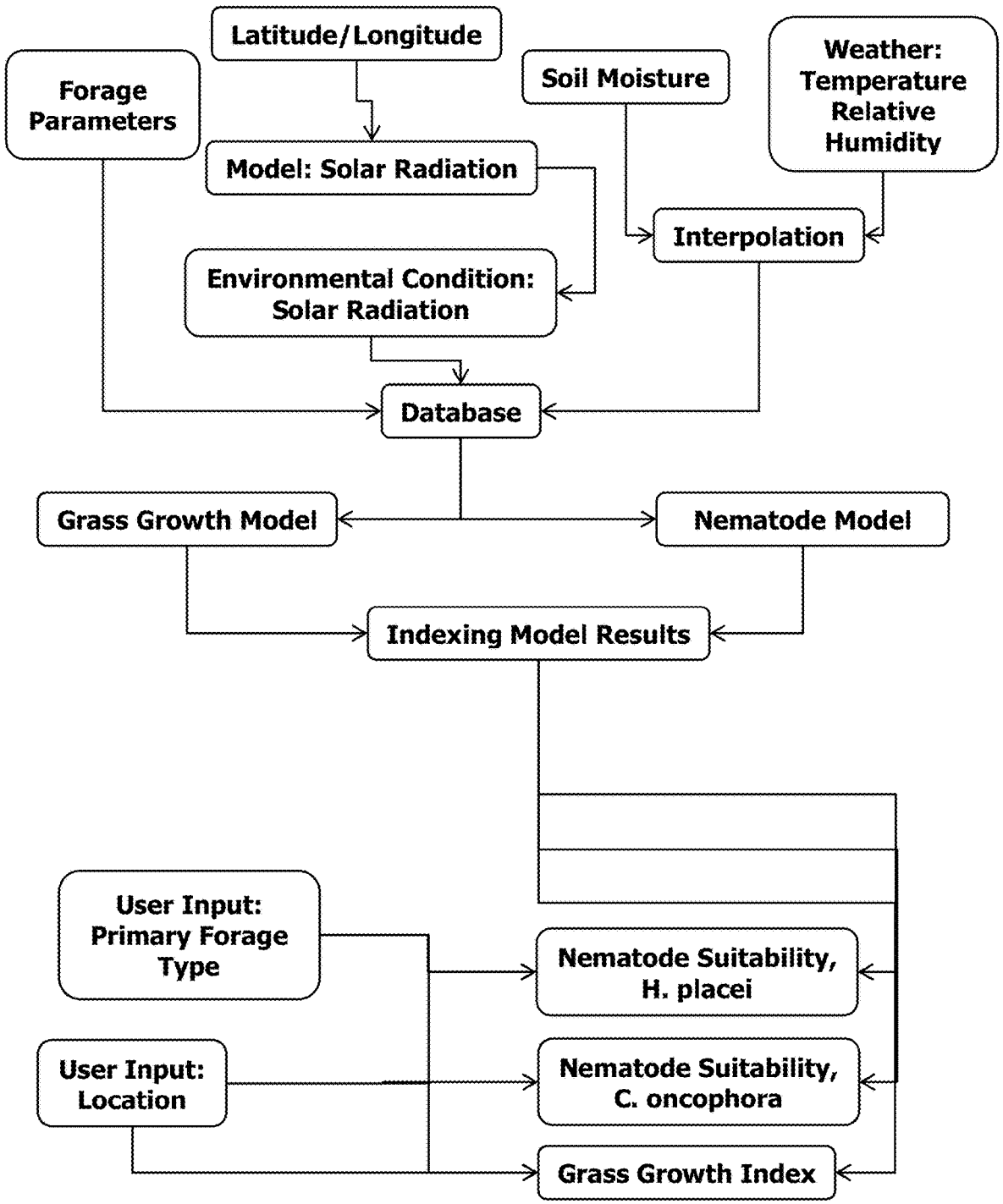
FIG. 1 is a flow chart showing the flow of data during practice of the disclosed method.
Figure 2:
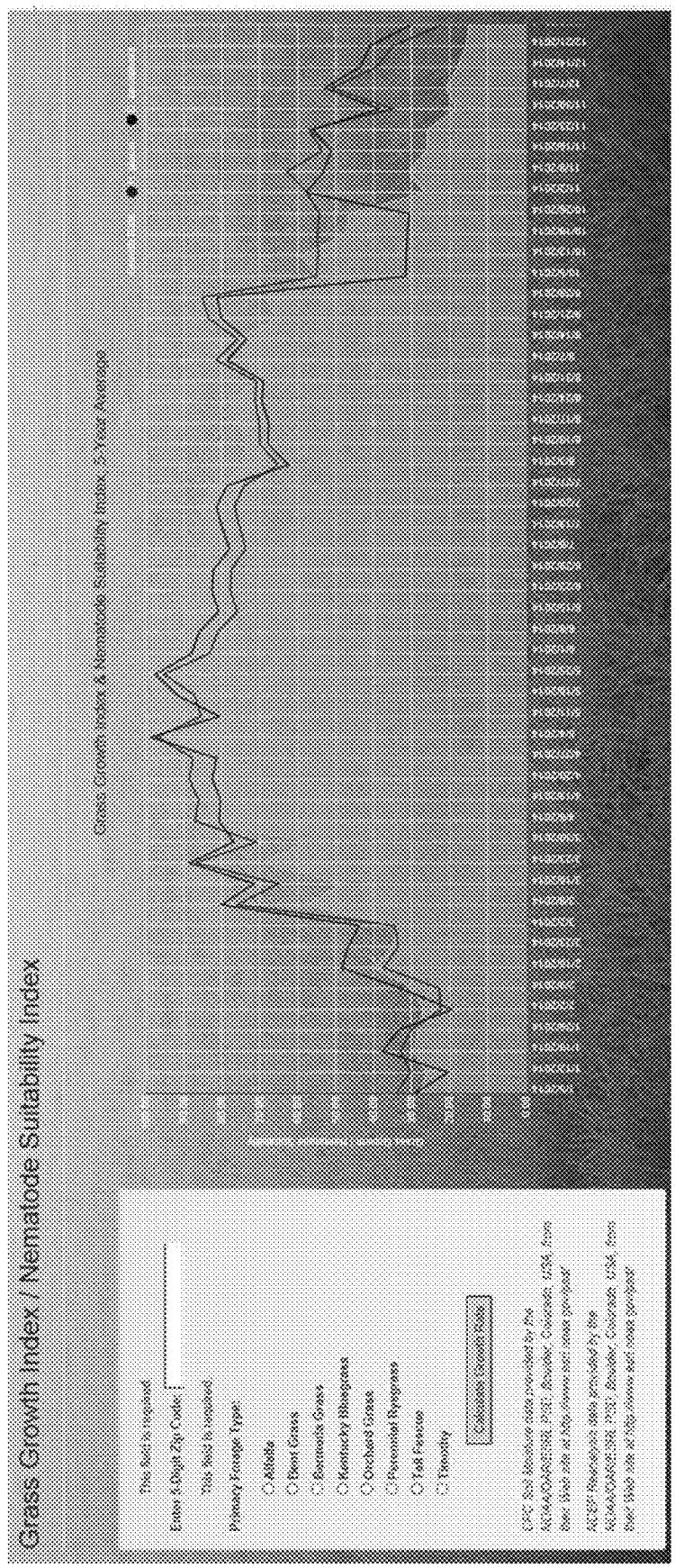
FIG. 2 is a representative screen shot of a user interface, including a visual output presented to a user in the practice of the disclosed method.

In an aspect, the invention provides a computer-implemented method of providing users with grass growth and nematode suitability indices, for the purpose of assisting the user with the determination of whether and when to administer parasiticides to grazing animals, such as bovines, ovines, caprines and the like, compromising: loading weather data in the form of daily mean surface-level temperature and daily mean surface-level humidity, loading environmental condition data in the form of soil moisture, loading location data in the form of a 0.5 degree latitude, longitude grid of the continental United States, and loading the growth parameters of eight different pasture forage types. Data is then loaded into a database which drives, assisted by user inputs, determination of the grass growth index and nematode suitability index.

Pasture forage parameters are loaded directly into the database. Location data is then entered into a model to calculate solar radiation so that when coupled with the time of year the amount of solar radiation is known for the entirety of the continental United States. The solar radiation data is then loaded into the database. The environmental condition of soil moisture as well as the weather data is then subjected to an interpolation method to increase the granularity of their gridded distribution. What was a 2.5×2.5 degree gridded dataset becomes a 0.5×0.5 degree gridded dataset. Following the interpolation it is then added to the database.

Once all data listed above is present in the database it is used to calculate, by county, the grass growth rates for eight different pasture forage types (Alfalfa, Bent Grass, Bermuda Grass, Kentucky Bluegrass, Orchard Grass, Perennial Ryegrass, Tall Fescue, and Timothy) and two different nematode species (*H. placei* and *C. oncophora*). To enable both the grass growth information and nematode information to share the same graphical axes, both numbers are scaled so their values fall between zero and 100. Following scaling, a complete dataset is prepared to be incorporated to a web application and accept user inputs.

The grass growth and nematode data act as a backend to a web-based application designed to accept user input and provide information regarding potential dosing of parasiticides for grazing cattle. The user inputs two parameters: location and pasture forage type. The location comes in the form of zip code and the pasture type is in the form of radio buttons from the options listed above. Once those two parameters are entered then a graph of the calendar year is produced.

In an embodiment, the invention provides a computer-implemented method for conveying to a user in need thereof a growth index and a nematode suitability index for a location, to assist said user in determining whether and when to treat a plurality of grazing animals with a suitable parasiticidal agent, the method comprising the steps of:
  (a) receiving over a communications network pasture location information and forage type information, and from a requestor indicating the location of at least one pasture on which animals susceptible to nematode infestation graze, and the type of forage upon which the animals graze;
  (b) converting the location information into geographic coordinates;
  (c) identifying weather data and environmental condition data associated with an area around the location;
  (d) identifying nematode growth parameters and forage type growth parameters;
  (e) calculating weather and environmental information associated with the area around the location;
  (f) calculating the growth index and the nematode suitability index associated with the location for at least one specific time period;
  (g) communicating the growth index and nematode suitability index to the requestor via the communications network or a second communications network, thereby conveying the two indices.

In one embodiment of the method the weather data comprises daily mean surface-level temperature and daily mean surface-level humidity; the environmental condition data comprises soil moisture; the location data comprises 0.5 to about degree latitude, longitude grid of the continental United States; the nematode growth parameters include nematode growth rates in various conditions of temperature and moisture; and the forage type growth parameters include forage growth rates in various conditions of temperature and moisture.

In another embodiment of the method, the step of communicating the report to the requestor is accomplished by providing the report in an electronic file downloadable to a client computer at the requestor's location. In one particular embodiment, the client computer is a mobile phone. In some embodiments, the computer is another portable or wearable device.

In another embodiment, the step of communicating the report to the requestor may be accomplished by delivering the report to a client computer at the requestor's location.

In another aspect, the invention provides a computer-implemented method for producing a grass growth index and a nematode suitability index, which indices are useful to assist a user in determining when to administer parasiticides to a plurality of animals, compromising the steps of:
  (a) providing weather data;
  (b) providing environmental condition data;
  (c) providing location data;
  (d) providing growth parameters of at least two different pasture forage types;
  (e) providing user inputs;
  (f) loading the information from steps a-e into a database; and
  (g) combining the data from steps a-d with user inputs from step e and subjecting the combined data to calculation to produce a grass growth index and a nematode suitability index; thereby providing the user with the indices.

In another aspect, the invention provides a method for providing a user with a grass growth index (GGI) and a nematode suitability index (NSI), which indices are useful to assist the user in determining when to administer parasiticides to a plurality of animals, compromising the steps of:
  (a) providing weather data;
  (b) providing environmental condition data;
  (c) providing location data;
  (d) providing growth parameters of at least two different pasture forage types;
  (e) providing user inputs;
  (f) loading the information from steps a-e into a database;
  (g) combining the data from steps a-d with the user inputs from step e and subjecting the combined data to calculation to produce a grass growth index and a nematode suitability index; and
  (h) displaying or otherwise providing the grass growth index and nematode suitability index to the user, thereby providing the user with the indices.

In an embodiment of the foregoing method, the weather data comprises daily mean surface-level temperature and daily mean surface-level humidity; the environmental condition data comprises soil moisture; the location data comprises 0.5 to about degree latitude, longitude grid of the continental United States; the growth parameters comprise the optimal temperature and moisture conditions of at least eight different pasture forage types; and the user inputs comprise the selection of any or both of the following: location and pasture forage type.

In another embodiment, the following steps are practiced in the following order:
  (a) loading the growth parameters into a database;
  (b) loading location data into a model to calculate solar radiation data; wherein the model provides the amount of solar radiation for any location in the continental United States;
  (c) loading the solar radiation data is into the database;
  (d) subjecting the soil moisture data and the weather data to an interpolation method to increase the granularity of their gridded distribution; wherein this step transforms an initial gridded distribution of 2.5×2.5 into 0.5×0.5 degree gridded dataset; and
  (e) loading the interpolated degree gridded dataset into the database.

In one embodiment of the method, the forage types comprise alfalfa, bent grass, Bermuda grass, Kentucky bluegrass, Orchard grass, perennial ryegrass, tall fescue, and Timothy; and, the nematodes comprise *H. placei* and *C. oncophora*.

In another embodiment, the method further comprising the following steps:
  (a) scaling the grass growth and nematode data such that their values fall between zero and 100, so they may be plotted on the same graphical axis;

(b) preparing a complete dataset, which includes the scaled data and all the other data provided, which is suitable for being incorporated into a web application, which is capable of receiving user inputs;
(c) providing information regarding potential dosing of parasiticides for livestock grazing upon user-specified:
  i. pasture-forage type;
  ii. location, in the form of zip code and the
(d) producing and displaying a graph of the calendar year populated with the growth and the nematode indices.

Example 1

Instructions to Build Grass Growth Index and Nematode Suitability Index

Part 1: Determination of the Grass Growth Index

In order to determine the Grass Growth Index for specific pasture types several pieces of information are necessary. First environmental data is needed: surface level temperature, surface level relative humidity, soil moisture. All three of these datasets were downloaded as gridded datasets from NOAA. Gridded datasets are datasets built upon highly sophisticated models to include all available data for a particular variable. The strength of using a gridded dataset is that it has very good coverage of data (usually covers all of North America, if not the world) and often times this may be the only freely available dataset for a certain variable. However, the gridded datasets often come in low resolution grids such as 2.5 degrees by 2.5 degrees. In some areas of the world 2.5 degrees can equal over 150 miles and a lot can change between 150 miles. To combat this problem of resolution after the datasets are downloaded it is necessary to interpolate the data down to a more granular level. 0.5 degrees by 0.5 degrees was chosen due to the trade-off between resolution and computation time/data capacities. In essence, a new grid of 0.5 degrees by 0.5 degrees is created and existing data is fit to the new points based upon proximity.

Once the environmental data has been gathered and interpolated it is necessary to calculate the next pieces of information. One of the most critical factors for grass is the amount of sunlight that it receives. The amount of sunlight a particular area of the earth receives is a function of the length of the day—the longer the day the greater the amount of sunlight. For our purposes, cloud coverage or other impediments of sunlight making it to the ground (such as trees, buildings, etc.) are ignored. The exact equation for the day length (D) is:

$$\theta = 0.2163108 + 2\tan^{-1}[0.9671396\tan[0.00860*J-186]]$$

$$\varphi = \sin^{-1}[0.39795\cos\theta]$$

$$D = 24 - \frac{24}{\pi}\cos^{-1}\left[\frac{\sin\frac{p\pi}{180} + \sin\frac{L\pi}{180}\sin\varphi}{\cos\frac{L\pi}{180}\cos\varphi}\right]$$

The next calculation necessary is potential evaporation (PET):

$$PET = 1.6\left(\frac{\text{Day Length}}{12}\right)*\left(\frac{\text{Number of Days}}{30}\right)*\left(\frac{10T_a}{I}\right)^\alpha$$

Once the calculations are made then individual forage parameters are necessary to complete the calculations. These parameters include the radiation use efficiency (RUE) of the pasture type (a number between 0 and 1) and the grass growth temperatures as seen below (T is temperature in Fahrenheit):

TABLE 1

Grass Growth Temperature (by forage type)
Grass Growth Temperature
*all degrees in Fahrenheit

| Temperature | Value |
|---|---|
| Alfalfa | |
| <46 | 0 |
| 46-75 | $-0.00123T^2 + 0.1835T - 5.835$ |
| 75-95 | $-0.00238T^2 + 0.35476 - 12.21429$ |
| >95 | 0 |
| Bent Grass | |
| <41 | 0 |
| 41-74.5 | $-0.000865T^2 + 0.129786T - 3.866$ |
| 74.5-86 | $-0.00696T^2 + 1.02957T - 37.09217$ |
| >86 | 0 |
| Bermudagrass | |
| <50 | 0 |
| 50-80 | $-0.00108T^2 + 0.17312T - 5.96774$ |
| 80-100 | $-0.00238T^2 + 0.37857T - 14.04762$ |
| >100 | 0 |
| Kentucky Bluegrass | |
| <35 | 0 |
| 35-60 | $-0.00154T^2 + 0.18615T - 4.63077$ |
| 60-80 | $-0.00238T^2 + 0.28333T - 7.42857$ |
| >80 | 0 |
| Orchardgrass | |
| <40 | 0 |
| 40-69 | $-0.00115T^2 + 0.15977T - 4.55172$ |
| 69-86 | $-0.00368T^2 + 0.51103T - 16.75735$ |
| >86 | 0 |
| Perennial Ryegrass | |
| <41 | 0 |
| 41-72.5 | $-0.00977T^2 + 0.142613T - 4.205$ |
| 72.5-86 | $-0.00593T^2 + 0.86519T - 30.57778$ |
| >86 | 0 |
| Tall Fescue | |
| <41 | 0 |
| 41-72.5 | $-0.000977T^2 + 142613T - 4.205$ |
| 72.5-90 | $-0.00346T^2 + 0.50563T - 17.45455$ |
| >90 | 0 |
| Timothy | |
| <41 | 0 |
| 41-75 | $-0.00084T^2 + 0.12689T - 3.78992$ |
| 75-86 | $-0.00909T^2 + 1.37273T - 50.8181$ |
| >86 | 0 |

Now that the instant disclosure has been made, the skilled person could add additional forage types through the exercise of routine knowledge and work. Once all of that has been calculated and collected then the grass growth rate equation can be calculated. It takes the form of:

{(RUE(37.6d(ω*sin φ*sin δ+cos φ*cos δ*sin ω)))*
(−0.00085J+1.026)*($g_{Temperature}$)*($g_{Soil\ Water}$)*c
(G)−{σ$_t$*S$_{Soil\ Water}$*f$_{t-1}$ $^1$Growth Rate}

REFERENCES

Duru, M., et al. (2008). Modelling above-ground herbage mass for a wide range of grassland community types. *Ecological Modelling*, 220, 209-225.

Forsythe, W. C., et al. (1995). A model comparison for day length as a function of latitude and day of year. *Ecological Modelling*, 80, 87-95.

McCall, D. G. & Bishop-Hurley, G. J. (2003). A pasture growth model for use in a whole-farm dairy production model. *Agricultural Systems*, 76, 1183-1205.

At a high level, the equation calculates a net grass growth rate: "amount growing"—"amount dying." Finally, the values for all the pasture types across all weeks in the year are scaled so that the maximum is 100 and the minimum is 0. Scaling is done to allow for only one y-axis when comparing differing variables such as grass growth and nematode suitability.

Part 2: Determination of the Nematode Suitability Index

The nematode suitability index (NSI) is an adaptation of Bolajoko et al., 2015 and takes the functional form of:

$$NSI = \left(\frac{\varphi}{2\mu_p}\right) * \left(\frac{d_e * d_h}{(\mu_e + d_e) * (\mu_{l3} + d_h)}\right)$$

Essentially, the NSI is equal to the fecundity of females divided by mortality rate within the host times development to L3 stage times the migration of L3 out of the host divided by the mortality rates within the host and outside the host.

To accomplish this calculation first environmental data must be collected such as temperature and precipitation. This data again originates from NOAA in gridded form. Therefore the data must be interpolated into a greater resolution as was done above.

Similar to above, additional data must be calculated based upon location. These variables include day length (see equation above) and potential evaporation (see equation above).

Finally, the mortality parameters were gathered from leading academic literature on the topic of nematodes Bolajoko et al., 2015 and Rose et al., 2015.

Upon completion of the calculation of the NSI for *H. placei* and *C. oncophora* these values were then scaled so that the maximum value was 100 and the minimum value was 0. Again, this was done so that these values as well as the grass growth values could be placed on the same y-axis allowing for clean consumption of the data by the viewer.

What is claimed:

1. A computer-implemented method for conveying to a user in need thereof a growth index and a nematode suitability index for a location, to assist said user in determining whether and when to treat a plurality of grazing animals with a suitable parasiticidal agent, the method comprising:
   (a) receiving over a communications network pasture location information and forage type information, and from a requestor indicating the location of at least one pasture on which animals susceptible to nematode infestation graze, and the type of forage upon which the animals graze;
   (b) converting the location information into geographic coordinates;
   (c) identifying weather data and environmental condition data associated with an area around the location;
   (d) identifying nematode growth parameters and forage type growth parameters;
   (e) calculating weather and environmental information associated with the area around the location;
   (f) calculating the growth index and the nematode suitability index associated with the location for at least one specific time period and;
   (g) communicating the growth index and nematode suitability index to the requestor via the communications network or a second communications network, thereby conveying the two indices.

2. The method of claim 1, wherein:
   (a) the weather data comprises daily mean surface-level temperature and daily mean surface-level humidity;
   (b) the environmental condition data comprises soil moisture;
   (c) the location data comprises 0.5 to about degree latitude, longitude grid of the continental United States;
   (d) the nematode growth parameters include nematode growth rates in various conditions of temperature and moisture;
   (e) the forage type growth parameters include forage growth rates in various conditions of temperature and moisture.

3. The method of claim 1, wherein the step of communicating the report to the requestor is accomplished by providing the report in an electronic file downloadable to a client computer at the requestor's location.

4. The method of claim 3, wherein the client computer is a mobile phone or other portable or wearable device.

5. The method of claim 3, wherein the step of communicating the report to the requestor is accomplished by delivering the report to a client computer at the requestor's location.

6. A computer-implemented method for producing a grass growth index and a nematode suitability index, which indices are useful to assist a user in determining when to administer parasiticides to a plurality of animals, compromising the steps of:
   (a) providing weather data;
   (b) providing environmental condition data;
   (c) providing location data;
   (d) providing growth parameters of at least two different pasture forage types;
   (e) providing user inputs;
   (f) loading the information from steps a-e into a database; and
   (g) combining the data from steps a-d with user inputs from step e and subjecting the combined data to calculation to produce a grass growth index and a nematode suitability index; thereby providing the user with the indices.

7. A method for providing a user with a grass growth index and a nematode suitability index, which indices are useful to assist the user in determining when to administer parasiticides to a plurality of animals, compromising the steps of:
   (a) providing weather data;
   (b) providing environmental condition data;
   (c) providing location data;
   (d) providing growth parameters of at least two different pasture forage types;
   (e) providing user inputs;
   (f) loading the information from steps a-e into a database;
   (g) combining the data from steps a-d with the user inputs from step e and subjecting the combined data to calculation to produce a grass growth index and a nematode suitability index; and (h) displaying or otherwise providing the grass growth index and nematode suitability index to the user, thereby providing the user with the indices.

8. The method of claim 7, wherein:
(a) the weather data comprises daily mean surface-level temperature and daily mean surface-level humidity;
(b) the environmental condition data comprises soil moisture;
(c) the location data comprises 0.5 to about degree latitude, longitude grid of the continental United States;
(d) the growth parameters comprise the optimal temperature and moisture conditions of at least eight different pasture forage types; and
(e) the user inputs comprise the selection of any or all of the following: location and pasture forage type.

9. The method of claim 8, comprising the following steps in the following order:
(a) loading the growth parameters into a database;
(b) loading location data into a model to calculate solar radiation data; wherein the model provides the amount of solar radiation for any location in the continental United States;
(c) loading the solar radiation data is into the database;
(d) subjecting the soil moisture data and the weather data to an interpolation method to increase the granularity of their gridded distribution; wherein this step transforms an initial gridded distribution of 2.5×2.5 into 0.5×0.5 degree gridded dataset; and
(e) loading the interpolated degree gridded dataset into the database.

10. The method of claim 9, wherein the forage types comprise alfalfa, bent grass, Bermuda grass, Kentucky bluegrass, Orchard grass, perennial ryegrass, tall fescue, and Timothy; and, the nematodes comprise *H. placei* and *C. oncophora*.

11. The method of claim 7, further comprising the following steps:
(a) scaling the grass growth and nematode data such that their values fall between zero and 100, so they may be plotted on the same graphical axis;
(b) preparing a complete dataset, which includes the scaled data and all the other data provided, which is suitable for being incorporated into a web application, which is capable of receiving user inputs;
(c) providing information regarding potential dosing of parasiticides for livestock grazing upon user-specified:
  i. pasture-forage type;
  ii. location, in the form of zip code and the
(d) producing and displaying a graph of the calendar year populated with the growth and the nematode indices.

* * * * *